United States Patent [19]

Selker et al.

[11] Patent Number: 5,501,229
[45] Date of Patent: Mar. 26, 1996

[54] CONTINUOUS MONITORING USING A PREDICTIVE INSTRUMENT

[75] Inventors: Harry P. Selker, Wellesley; John L. Griffith, Natick, both of Mass.

[73] Assignee: New England Medical Center Hospital, Boston, Mass.

[21] Appl. No.: 283,951

[22] Filed: Aug. 1, 1994

[51] Int. Cl.$^6$ .................................................. A61B 5/04
[52] U.S. Cl. ...................................... 128/696; 364/413.06
[58] Field of Search ................................... 128/696, 702, 128/703, 704, 705; 364/413.06

[56] References Cited

U.S. PATENT DOCUMENTS

| 3,608,545 | 9/1971 | Novak et al. |
| 3,937,004 | 2/1976 | Natori et al. |
| 4,181,135 | 1/1980 | Andresen et al. |
| 4,230,125 | 10/1980 | Schneider |
| 4,315,309 | 2/1982 | Coli |

(List continued on next page.)

FOREIGN PATENT DOCUMENTS 599407  11/1987  Australia .................. A61B 5/04

OTHER PUBLICATIONS

Cohen et al., "Automated Electroencephalographic Analysis As A Prognositc Indicator In Stroke", Medical and Biological Engineering & Computing 431–437 (Jul. 1977).
Gillum et al., "International Diagnositc Criteria For Acute Myocardial Infarction And Acute Stroke", Progress In Cardiology, American Heart Journal 150–158 (Jul. 1984).
Harvey et al., "1985 Yearbook of Cardiology", pp. 170–173.
Krucoff et al., "Noninvasive Detection Of Coronary Artery Patency Using Continuous ST–Segment Monitoring", American Journal of Cardiology 1986; 57:916–922.
Krucoff et al., "The Portable Programmable Microprocessor–Driven Real–Time 12–Lead Electrocardiographic Monitor: A Preliminary Report Of a New Device For The Noninvasive Detection Of Successful Reperfusion or Silent Coronary Reocclusion", American Journal of Cardiology 1990; 65:143–148.
Krucoff et al., "Heuristic And Logistic Principles Of ST–Segment Interpretation In The Time Domain", Journal of Electrocardiology vol. 23 supplement (pp. 6–10).
Long et al., "A Comparison Of Logistic Regression To Decision–Tree Induction In A Medical Domain", Computers And Biomedical Research 26, 74–97 (1993).
Pozen et al., "A Predictive Instrument To Improve Coronary–Care–Unit Admission Practices In Acute Ischemic Heart Disease", New England Journal of Medicine; 310:1273–1278 (May 1984).
Cardiology Update, Review For Physicians, 1986 Edition by Elliot Rappaport, "Thrombolysis In Accute Myocardial Infarction", by Sherman et al., pp. 117–135.

Primary Examiner—William E. Kamm
Assistant Examiner—Scott M. Getzow
Attorney, Agent, or Firm—Fish & Richardson

[57] ABSTRACT

An instrument for continuously monitoring the condition of a patient who has a cardiovascular disease, the instrument including an electrocardiograph; a waveform analyzer which analyzes a current segment of an ECG waveform; a computer receiving output from the waveform analyzer; and a control module. The computer is programmed to complete a monitoring cycle in which the computer uses the output from the waveform analyzer to compute a probability of a life threatening cardiac condition based upon the current segment of the patient's ECG waveform. The control module causes the computer to periodically repeat the monitoring cycle and for each repetition of said monitoring cycle to compute a change-of-condition measure, wherein the change-of-condition measure is calculated by subtracting a computed probability for a previous monitoring cycle from the computed probability for the current monitoring cycle. The computer is also programmed to compare during each monitoring cycle the computed change-of-condition measure for that monitoring cycle to a threshold value and if in excess of the threshold value to generate an alarm notification.

10 Claims, 2 Drawing Sheets

U.S. PATENT DOCUMENTS

| | | |
|---|---|---|
| 4,347,851 | 9/1982 | Jundanian . |
| 4,404,974 | 9/1983 | Titus . |
| 4,422,081 | 12/1983 | Woods . |
| 4,457,315 | 7/1984 | Bennish . |
| 4,610,254 | 9/1986 | Morgan et al. . |
| 4,664,125 | 5/1987 | Pinto . |
| 4,679,144 | 7/1987 | Cox et al. ............... 364/417 |
| 4,680,708 | 7/1987 | Ambos et al. ............. 364/417 |
| 4,754,762 | 7/1988 | Stuchl ..................... 128/696 |
| 4,893,270 | 1/1990 | Beck et al. ............... 364/900 |
| 4,945,477 | 7/1990 | Edwards ................ 364/413.06 |
| 4,957,115 | 9/1990 | Selker ..................... 128/696 |
| 4,974,598 | 12/1990 | John ....................... 128/696 |
| 4,998,535 | 3/1991 | Selker et al. ............. 128/696 |
| 5,046,499 | 9/1991 | Berger ..................... 128/654 |
| 5,054,493 | 10/1991 | Cohn et al. ............... 128/672 |
| 5,276,612 | 1/1994 | Selker ................... 364/413.06 |

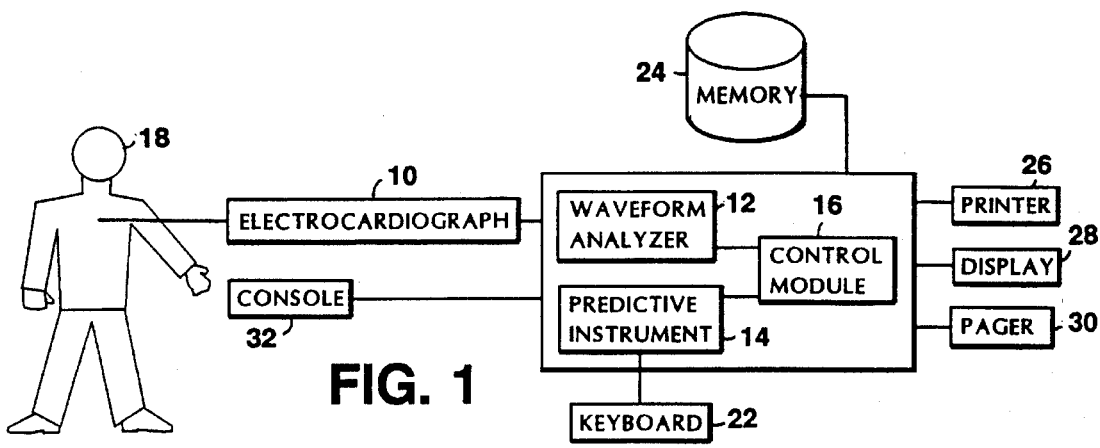
FIG. 1
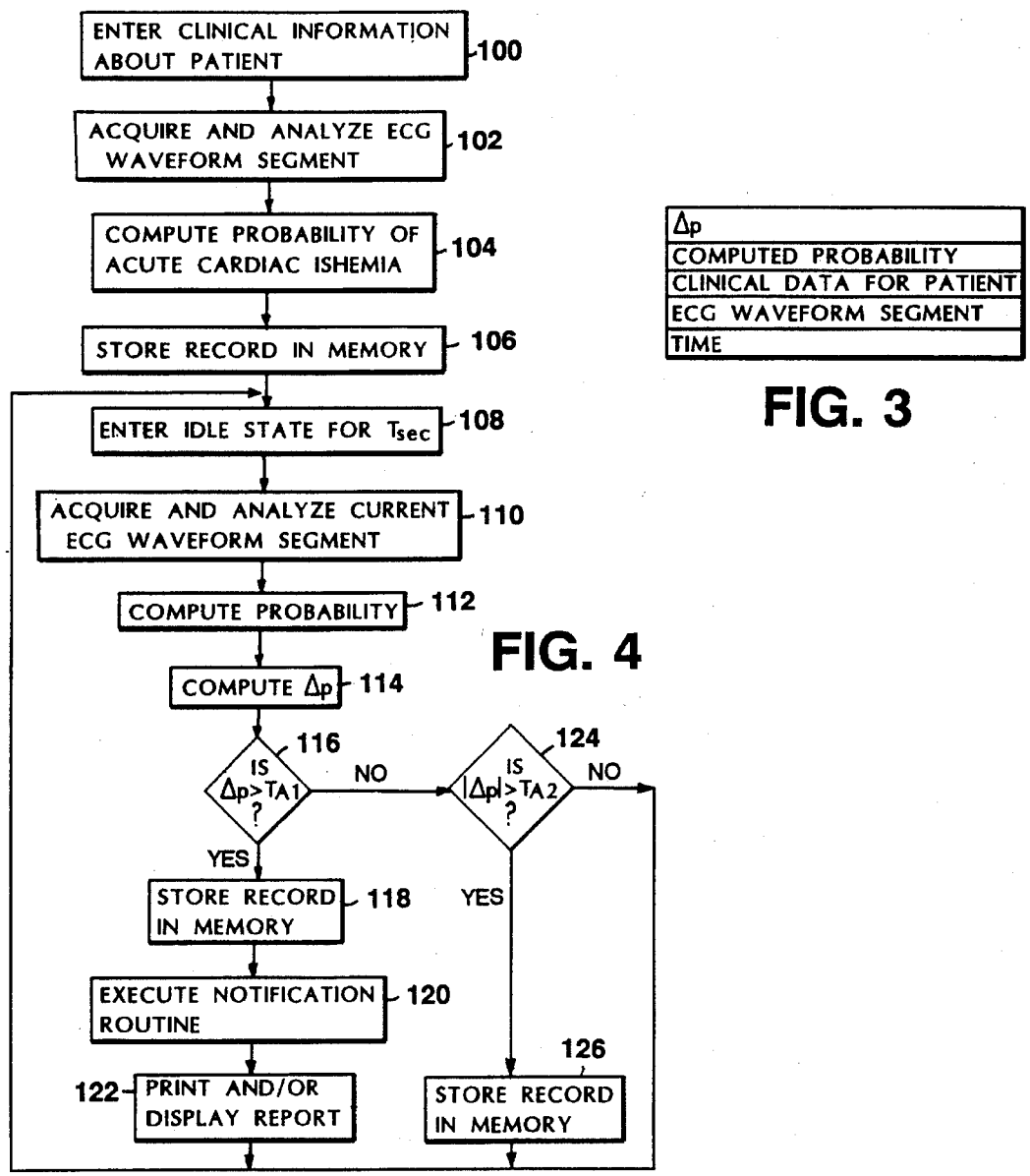
FIG. 3
FIG. 4

| Variable | Coefficients ($b_i$) | | Values ($x_i$)[a] |
|---|---|---|---|
| CONSTANT ($b_0$) | -3.933 | | |
| CPAIN | 1.231 | chest of left arm pain/pressure present | 1 |
| | | not present | 0 |
| SX1CPAIN | 0.882 | chest or left arm pain chief complaint | 1 |
| | | otherwise | 0 |
| MALESEX | 0.712 | male | 1 |
| | | female | 0 |
| AGE 40 | -1.441 | patient age 40 yrs or less | 1 |
| | | otherwise | 0 |
| AGE50 | 0.667 | patient age greater than 50 yrs. | 1 |
| | | otherwise | 0 |
| SEXAGE50 | -0.426 | male patient age greater than 50 yrs | 1 |
| | | otherwise | 0 |
| QWAVE | 0.616 | ECG Q waves present | 1 |
| | | otherwise | 0 |
| STEL | 1.314 | ECG S-T segment elevated 2 mm or more | 2 |
| | | ECG S-T segment elevated 1-2 mm | 1 |
| | | otherwise | 0 |
| STDEP | 0.993 | ECG S-T segment depressed 2 mm or more | 2 |
| | | ECG S-T segment depressed 1-2 mm | 1 |
| | | ECG S-T segment depressed 0.5-1.0 mm | 0.5 |
| | | otherwise | 0 |
| TWEL | 1.095 | ECG T-waves elevated ("hyperacute) | 1 |
| | | otherwise | 0 |
| TWINV | 1.127 | ECG T-waves inverted 5 mm or more | 2 |
| | | ECG T-waves inverted 1-5 mm | 1 |
| | | ECG T-waves flat | 0.5 |
| | | otherwise | 0 |
| TWISTDEP | -0.314 | Both STDEP and TWINV not 0 | 1 |
| | | otherwise | 0 |

FIG. 2

CONTINUOUS MONITORING USING A PREDICTIVE INSTRUMENT

BACKGROUND OF THE INVENTION

The invention relates to predictive instruments for computing a patient's probability of a serious cardiac condition.

A number of instruments have been developed that enable the physician to compute probabilities of life threatening cardiac conditions for patients. Some of these instruments are described in the following references, all of which are incorporated herein be reference.

A hand-held predictive instrument is described by Michael W. Pozen et al. in "A Predictive Instrument to Improve Coronary-Care-Unit Admission Practices in Acute Ischemic Heart Disease" The New England Journal of Medicine, Vol 310 pp. 1273–1278, May 17, 1984. With the handheld calculator-based instrument, a physician can compute a patient's probability of having acute cardiac ischemia based upon physician-entered values for a set of clinical variables. An automatic, computerized version of this instrument which utilizes output from a electrocardiograph and a waveform analyzer is described by H. P. Selker et al. in "A Time-Insensitive Predictive Instrument for Acute Myocardial Infarction Mortality", Med. Care 1991; 29:1196–1211.

A predictive instrument for determining the probability of acute hospital mortality of a cardiac patient is described in U.S. Pat. No. 4,957,115 to Dr. Harry P. Selker. The probability of acute hospital mortality is commonly understood to mean the probability of dying from a current acute condition, generally during the specific initial hospitalization for the problem. It is also referred to as the probability of imminent death for the patient. That is, it is a short term, as opposed to a long term, probability of mortality which does not necessarily have a precisely defined period of time associated with it.

A predictive instrument for evaluating whether to use thrombolytic therapy to treat a patient with a heart condition is described in U.S. Pat. No. 4,998,535 to Dr. Selker et al. The predictive instrument computes a first probability of acute hospital mortality for the patient assuming that thrombolytic therapy is not administered and it computes a second probability of acute hospital mortality for the patient assuming that thrombolytic therapy is administered. The difference in the computed probabilities may assist the physician in deciding whether it would be advantageous to administer the thrombolytic therapy to the patient.

The above-mentioned predictive instruments use logistic regression equations to model the probability that the patient has a serious cardiac condition (e.g. the probability of acute cardiac ischemia or the probability of imminent death from a cardiac condition).

SUMMARY OF THE INVENTION

In general in one aspect, the invention is an instrument for continuously monitoring the condition of a patient who has a cardiovascular disease. The instrument includes an electrocardiograph; a waveform analyzer which analyzes a current segment of an ECG waveform for the patient; a computer receiving output from the waveform analyzer; and a control module. The computer is programmed to complete a monitoring cycle in which the computer uses the output from the waveform analyzer to compute a probability of a life threatening cardiac condition based upon the current segment of the patient's ECG waveform. The control module causes the computer to periodically repeat the monitoring cycle and for each repetition of the monitoring cycle to compute a change-of-condition measure. The change-of-condition measure is calculated by subtracting a computed probability for a previous monitoring cycle from the computed probability for the current monitoring cycle. The computer is also programmed to compare during each monitoring cycle the computed change-of-condition measure for that monitoring cycle to a threshold value and if in excess of said threshold value to generate an alarm notification.

Other advantages and features will become apparent from the following description of the preferred embodiment and from the claims.

BRIEF DESCRIPTION OF THE DRAWINGS

FIG. 1 is a block diagram of a patient monitoring system constructed in accordance with the invention;

FIG. 2 presents the coefficients and variables of an example of a logistic regression equation used to predict a particular cardiac outcome, e.g. the probability of acute cardiac ischemia;

FIG. 3 is a flow chart showing the operation of the system shown in FIG. 1; and

FIG. 4 shows the record data structure which the control module stores in memory.

DESCRIPTION OF THE PREFERRED EMBODIMENTS

Referring to FIG. 1, a cardiac patient monitoring system constructed in accordance with the invention includes a 12-lead electrocardiograph 10, a waveform analyzer 12, a predictive instrument 14, and a control module 16. Electrocardiograph 10 is connected to a patient 18 and produces a set of ECG waveforms for the patient. Waveform analyzer 12 is programmed to analyze the ECG waveforms and recognize the presence of certain characteristics that are particularly indicative of the cardiac condition of the patient, e.g. the presence and elevation or depression of S-T segments, the presence Q waves, and the presence of elevated, depressed or inverted T-waves. The particular characteristics which the waveform analyzer is programmed to recognize depend upon the function that is performed by the predictive instrument which in turn determines the set of clinical variables that are required to perform that function. Predictive instrument 14 uses the output of waveform analyzer 12 in conjunction with other clinical information about the patient that has been entered by a physician through a keyboard 22 and computes a probability that the patient has a life-threatening cardiac condition. Control module 16 controls the operation of the other components in the system, detects a change in the computed probability patient's condition, and takes appropriate actions when the detected change exceeds certain thresholds, e.g. storing the measurements in a digital memory 24 (e.g. RAM or disk storage), printing a report out on a printer 26 attached to the system, displaying the report on a video screen 28, or notifying medical support staff when the patient's condition has deteriorated significantly (e.g. by using a pager 30 to send a page to the physician).

Electrocardiograph 10 and waveform analyzer 12 are commercially available as a single unit. For example, Hewlett Packard makes the HP Pagewriter XLi which is a mobile unit that can be moved from one patient to the next. The Pagewriter XLi includes a built-in 80386-based computer that can be programmed to perform the appropriate waveform analysis. For example, it can be programmed to recognize and quantify the presence of key features within the ECG waveform. It can also be programmed to identify the location of a myocardial infarction (MI) based on the characteristics of the set of signals produced by the twelve monitoring leads. Besides performing the wave analysis functions, the computer within the unit can also be programmed to perform the functions of other components or modules within the system, e.g. the computations of the predictive instrument and the functions of the control module.

In the described embodiment, predictive instrument 14 is an ACI-TIPI (Acute Cardiac Ischemia Time-Insensitive Predictive Instrument) which uses a logistic regression-based equation for computing the probability that the patient is experiencing acute cardiac ischemia. The logistic regression equation is of the form:

$$P = 100 \left[ 1 - \frac{1}{1 + e^{b_0 + \Sigma b_i x_i}} \right]$$

where P is the probability of acute cardiac ischemia, $b_0$ is a constant, and the $b_i$'s are coefficients of the variables $x_i$ which are included in the model.

The variables which are used in this equation are shown in FIG. 2 along with the values of the coefficients and the values which the $x_i$'s can take for the different variables. Note that only the largest value for x is used per variable. Also ECG findings must be present in at least two leads, and S-T segment and T wave changes are "normal" if secondary to right or left complete bundle branch blocks, left ventricular hypertrophy, or a paced QRS. Only one type of abnormality is coded each for S-T segment and for T wave per patient (exclusive of TWISTDEP), use with elevation taking priority. Deviations are expressed in mm using the standard ECG scale of 1 mm=0.1 mV.

The system is programmed to operate in the manner shown in FIG. 3. When the patient is first connected to the system, the physician enters the relevant clinical information about the patient (step 100). For example, if the predictive instrument is programmed to compute the probability of acute cardiac ischemia in accordance with the above model, the physician enters the following information about the patient: (1) name; (2) age; (3) sex; (4) whether the patient is experiencing chest or left arm pain; and (5) whether the patient's chief complaint is chest or left arm pain. After the physician has set up the system for a particular patient and connects the leads of the electrocardiograph to the patient, the physician causes the system to perform an initial ECG for the patient. In response, the waveform analyzer acquires and analyzes a current segment of the patient's ECG waveform (step 102). Typically, a 10–20 second segment of the patient's ECG is required by the waveform analyzer to perform its waveform analysis functions. The output of the waveform analyzer passes to the predictive instrument, which may, for example, be implemented by a computation routine within the computer. In the present embodiment, the output of the waveform analyzer reports whether: (1) any Q waves are present; (2) whether the S-T segment is elevated or depressed and by how much; (3) whether the T-waves are elevated inverted or flat; (4) if the T-waves are elevated, by how much; and (5) whether both the STDEP and TWINV leads are non-zero.

Using the output of the waveform analyzer and previously entered values for other clinical variables, the predictive instrument computes a probability that the patient has acute cardiac ischemia (step 104). The control module then stores a record of the computation in memory (step 106). Referring to FIG. 4, the record includes the computed probability along with the underlying clinical information, the ECG waveforms from which the probability was generated, and a time-stamp indicating when the measurement was performed.

Thereafter, the control module enters a monitoring mode in which it periodically executes a monitoring cycle. At the beginning of each monitoring cycle the system enters an idle state for a user-selectable period of time, $T_{sec}$ (step 108). At the end of the idle period, the control module causes the waveform analyzer to acquire and analyze a segment of the current ECG waveform and pass its results to the predictive instrument (step 110). The predictive instrument then computes an updated probability for the patient based on the patient's current ECG waveform (step 112). The control module computes $\Delta_p$ which is measure of the change (or delta) in the patient's condition since the last recorded monitoring cycle (step 114). In the described embodiment, $\Delta_p$ is equal to the proportional change in the computer probability $$\left( \text{i.e., } \Delta_P = \frac{P_{new} - P_{last}}{P_{last}} \right),$$

where $P_{last}$ equals the last recorded probability and $P_{new}$ equals the current computed probability.

The control module compares the computed change statistic $\Delta_p$ to a first threshold $T_{A1}$, which represents an alarm threshold or the threshold for clinical activity (step 116). That is, changes that are larger than $T_{A1}$ are considered to be significant enough to deserve the immediate attention of medical staff. If $\Delta_p$ exceeds $T_1$, the control module stores in memory a record containing the value of the newly computed probability, the value of $\Delta_p$, the underlying clinical information, the corresponding ECG waveform, and a time-stamp indicating when the measurement was performed (step 118). The control module also executes a notification routine which notifies medical staff of the patient's worsening condition (step 120). The notification may be in any one or more of many possible forms. For example, the notification routine might cause a page to be sent to the responsible physician, it might generate an audible alarm at the location of the mobile monitoring unit, it might send a message to the central nursing station which would appear on a central display monitor and also trigger an audible alarm at the nurse's station, or it might perform any combination of those or similar actions.

After the control module has executed the notification routine, it displays and/or prints a report of the computed probability, the underlying ECG waveforms and a history of the computed probabilities over a selected period of time prior to the most recent monitoring cycle (step 122). The control module then causes the system to enter the idle state for the preselected delay period or until the patient or medical staff enters new clinical information reflecting a change in the patient's condition.

In the event that $\Delta_p$ is not greater than $T_{A1}$, the control unit compares the absolute value of $\Delta_p$ to a lower threshold $T_{A2}$ (step 124). Threshold $T_{A2}$ defines a level below which the change in the patient's condition is considered to be not large enough to be clinically significant. If $\Delta_p$ exceeds $T_{A2}$, the control module stores a record of the measurement including the computed probability, $\Delta_p$, the underlying data, the ECG waveform, and a time-stamp indicating when the measurement was performed (step 126). This record then defines the reference from $\Delta_p$ is computed for the next computed probability.

Threshold $T_{A2}$ is set so that the system will generate a history of the patient's condition containing records of only the clinically meaningful events. Using the second threshold as a criteria for storing monitoring data greatly reduces the amount of information that is stored by the monitoring system. Thus, the limited system memory is not filled with clinically redundant information.

After a monitoring cycle is complete, the system returns to an idle state for the preselected period of time. Then, it begins a new monitoring cycle. The above-described sequence repeats until the user terminates it.

As alluded to above, it is possible to manually trigger a monitoring cycle by entering new values for relevant clinical variables. For example, if the patient begins to experience chest pain, he can enter this new information through a bedside console 32 (see FIG. 1), or alternatively, medical staff can enter it through another input device. Entering the changed clinical information causes the control unit to immediately initiate a new monitoring cycle immediately or, if it is currently in the middle of a monitoring cycle, to initiate a monitoring cycle immediately after it has completed the current monitoring cycle.

The system also has a manual mode of operation in which the probability is computed only when medical staff manually initiates a new monitoring cycle by, for example, pushing an appropriate button on the bedside control console. In all other respects, the monitoring cycle which is initiated is the same as the monitoring cycle described above.

It should be noted that the thresholds, $T_{A1}$ and $T_{A2}$, may be simple fixed value thresholds or they may be functions of some other variable, such as $P_{last}$. For example, with regard to $T_{A1}$ it may be desirable to have this value set higher for smaller values of $\Delta_p$ than for larger values of $\Delta_p$. In other words, a 25% increase from an initial probability of 5% would probably not be significant whereas a 25% increase from an initial probability of 40% would probably provide a basis for real concern.

In addition, the thresholds can be a function of previous computed changes. For example, two successive $\Delta_p$'s both indicating a worsening condition provide a greater basis for concern than does a sequence of $\Delta_p$'s that alternate between positive and negative values. In other words, the threshold could be set as a function of the direction (or sign) of computed change for previous monitoring cycles. If the previous computed value for $\Delta_p$ was positive (e.g. indicating a worsening condition), the threshold for the next computed value of $\Delta_p$ might be lower than it would be if the previous computed value for $\Delta_p$ was negative.

Also $\Delta_p$ can be defined in any of a number of alternative ways. For example, it can be a rate of change computed by the change from the last recorded clinically meaningful event divided by the time difference between the current measurement and the last recorded measurement. Alternatively, it can simply be an absolute change (i.e., $P_{new} - P_{last}$).

The logistic regression equation presented above is presented as merely illustrative of one way in which the cardiac condition and the probability can be modeled. There are a variety of statistical methods and algorithms that can be used for calculating the predicted probability of an adverse cardiac event or a life threatening cardiac condition. These include, for example, artificial feed-forward multilayer neural networks and classification trees. Although the procedures may differ among these various techniques, many of them may generally be expressed in terms of finding an optimal solution to the following general equation:

$$f^{-1}(\text{probability of event}) = \beta_0 + \sum_{i=1}^{K} \beta_i g_i(X_1, X_2, \ldots X_p),$$

where $f^{-1}$ and $g_i$ are general functions, the $X_n$'s (where $1 \leq n \leq p$) are the values of the independent input variables, and $\beta_0$ and $\beta_i$ (where $1 \leq i \leq K$) are model coefficients.

The standard logistic regression equation described earlier can be derived from the above equation. In addition an artificial network with a single hidden layer and an activation function "h" can be written as:

$$f^{-1}(\text{output}) = \beta_0 + \sum_{i=1}^{K} \left\{ \beta_i h \left( \sum_{j=1}^{p} \alpha_{ij} X_j \right) \right\}.$$

The automatic, periodic monitoring of the patient's condition with the predictive instrument provides information that assists the physician in more accurately evaluating the seriousness of the patient's condition and in obtaining early detection of changes in the patient's condition. The advantages are illustrated by the following actual histories of four patients, identified as Patient A, Patient B, Patient C, and Patient D.

Patient A presented at the ED (Emergency Department) with a potentially life-threatening cardiac rhythm. The first computed probability of acute cardiac ischemia (i.e., either unstable angina pectoris or acute myocardial infarction, as opposed to a rhythm disturbance) was relatively low, at 10%. In a subsequent ECG taken 23 minutes later, the cardiac rhythm had returned to normal, which would lead to a conclusion of no remaining cardiac problem. Indeed, a usual ECG monitor would have shown the patient as having a normal rhythm and an essentially normal ECG. However, the ECG contained a relatively minor ST elevation in the anterior leads which caused the computed probability of acute cardiac ischemia to rise to 16%, representing a 60% increase from the previous computed probability. An increase of that amount flagged the patient as having acute cardiac ischemia and still requiring acute medical attention.

An interesting aspect of this example is that both of the computed probabilities are below the level at which patients are commonly sent home, which in the facility in which this patient was treated, is about 18%. Thus, a computed probability of 16% by itself is difficult to interpret because the physician does not know whether that is a normal reading for that patient. Just being of a certain age and gender and having chest pains can often result in more than 16% probability with no abnormality in ECG.

To more fully appreciate the significance of a computed probability of 16%, it is useful to explore what the figure actually means. A 16% reading indicates that among a representative population of 100 patients, all of whom arrive at the ED with presenting conditions that produce a probability of 16%, on average 16 of the patients will have acute ischemia and 84 patients will not have acute ischemia. Within that population, however, the predictive instrument based upon a single computation is not able to distinguish between the group of patients who have acute ischemia and the group of patients who do not have acute ischemia. By using the predictive instrument in accordance with the above-described invention, the physician is able to discover further information which will assist the physician in determining to which group the patient actually belongs.

By monitoring the change in the patient's computed probability, the physician was able to gain further information which helped interpret the initial reading of 10%. That is, the instrument detected a substantial change in the computed probability in a direction that flagged the patient as being more likely to fall within that category of patients who have acute ischemia.

In the case of Patient B, he arrived at the ED with a chest pain as his chief complaint. His initial computed probability of acute cardiac ischemia was 25%. However, chest pain in a properly aged male, who does not have acute cardiac ischemia, can still produce a relatively high probability. In other words, one can obtain that same probability in a variety of different ways, not all of which are symptomatic of acute cardiac ischemia. Thus, even though the presenting probability of 25% is a relatively high number, by itself its meaning to the physician is still ambiguous. It simply indicates that the patient falls into a category of patients who have historically exhibited higher risk than the group of patients who have generated lower computed probabilities. From the physician's perspective the predictive instrument is indicating that the patient has a one-in-four chance of having acute cardiac ischemia but the instrument is also indicating that the patient has a three-in-four chance of not having acute cardiac ischemia.

In the case of Patient B, a second ECG approximately one hour later still appeared to be relatively normal and again produced a computed probability of acute cardiac ischemia of 25%. However, in a subsequent electrocardiogram taken about two hours after the initial ECG, there were very subtle changes of lateral T wave flattening that produced a computed probability of 37%, clearly flagging the patient as requiring clinical activity. Such subtle changes would not have been flagged except for the fact that the predictive instrument magnifies any changes of this type. Thus, because the predictive instrument when used in a continuous manner amplifies the seemingly most trivial of changes in the patient's condition, it can give the physician further valuable information which will help him or her to accurately evaluate the patient's condition and make the correct admission decision.

Patient C, a woman with known cardiac problems, came into the ED with general complaint about not feeling well. When the monitor was connected to her, the computed probability was 10%. Nevertheless, because of her history of known problems she was admitted to the ward. While she was in the ward, she began to experience chest pains which caused the computed probability to jump up to 50%, an increase of about 400%, clearly flagging her for immediate clinical action.

Patient D, a 64 year old woman, represents yet another example of the invention's ability to help medical staff distinguish among patient's who have acute cardiac ischemia and those who do not. The patient's initial ECG was benign and the computed probability indicates only a 4% likelihood of acute cardiac ischemia. She was admitted to the ward because she was known to have bad coronary disease. In a subsequent ECG taken about 22 hours later, suddenly the very same ECG, coupled with a new chief complaint of chest pain, resulted in a six-fold increase in the probability of acute cardiac ischemia (i.e., 24%). In this case, the actual ECG was unchanged and thus a normal ECG heart monitor would not have picked up the significance of the new information. Moreover, this patient's final number (i.e., 24%) was below average for patients in the ED and, in fact, was within the range of numbers for patients who are sent home. However, because the delta (i.e., change in computed probability) was substantial she was flagged as a patient requiring further clinical activity.

Other embodiments are within the following claims. Even though the monitoring of the probability of acute cardiac ischemia for changes was used as an example, this was not meant to limit the scope of the invention to only those systems which compute that particular probability. The invention also encompasses systems which periodically compute and monitor for changes any probability of a serious cardiac condition. In addition, the method by which the probability is not computed is not central to the invention. Any approach which attempts to model historical patient information to compute a probability of the patient having a serious cardiac condition based at least in part upon ECG information falls within the scope of this invention.

What is claimed is:

1. An instrument for continuously monitoring the condition of a patient who has a cardiovascular disease, said instrument comprising:

an electrocardiograph which during use is connected to the patient;

a waveform analyzer which analyzes a current segment of an ECG waveform for the patient from the electrocardiograph;

a computer receiving output from the waveform analyzer, said computer programmed to complete a monitoring cycle in which the computer uses the output from the waveform analyzer to compute a probability of a life threatening cardiac condition based upon the current segment of the patient's ECG waveform; and a control module causing said computer to periodically repeat the monitoring cycle and for each repetition of said monitoring cycle to compute a change-of-condition measure, wherein said change-of-condition measure is calculated by subtracting a computed probability for a previous monitoring cycle from the computed probability for the current monitoring cycle, said computer further programmed to compare during each monitoring cycle the computed change-of-condition measure for that monitoring cycle to a threshold value and if in excess of said threshold value to generate an alarm notification.

2. The instrument of claim 1 further comprising a computer readable data storage unit and wherein said computer is programmed to store in said data storage unit the computed probability and data on which said computed probability is based only when said computed change-of-condition measure exceeds a second threshold.

3. The instrument of claim 1 further comprising an input device for entering clinical information relating to the patient and wherein said computer uses the output from the waveform analyzer as well as the clinical information entered through said input device to compute the probability of a life threatening cardiac condition.

4. The instrument of claim 1 wherein the probability of a life threatening cardiac condition is a probability that the patient has acute cardiac ischemia.

5. The instrument of claim 1 wherein the probability of a life threatening cardiac condition is a probability of acute hospital mortality for the patient.

6. The instrument of claim 1 wherein the computer uses a logistic regression equation to compute the probability of a life threatening cardiac condition.

7. The instrument of claim 1 wherein the control module is programmed to cause said computer to repeat the monitoring cycle at regular intervals separated by a preselected delay.

8. The instrument of claim 7 wherein the preselected delay is user selectable.

9. An instrument for continuously monitoring the condition of a patient who has a cardiovascular disease, said instrument comprising:

an electrocardiograph which during use is connected to the patient;

a waveform analyzer which analyzes a current segment of a ECG waveform for the patient from the electrocardiograph;

a computer receiving output from the waveform analyzer, said computer programmed to complete a monitoring cycle in which the computer uses the output from the waveform analyzer to compute a probability of a life threatening cardiac condition based upon the current segment of the patient's ECG waveform; and a control module which responds to a user-entered command by causing said computer to execute the monitoring cycle and for each repetition of said monitoring cycle to compute a change-of-condition measure, wherein said change-of-condition measure is calculated by subtracting a computed probability for a previous monitoring cycle from the computed probability for the current monitoring cycle, said computer further programmed to compare during each monitoring cycle the computed change-of-condition measure for that monitoring cycle to a threshold value and if in excess of said threshold value to generate an alarm notification.

10. An instrument for continuously monitoring the condition of a patient who has a cardiovascular disease, said instrument comprising:

an electrocardiograph which during use is connected to the patient;

a waveform analyzer which analyzes a current segment of a ECG waveform from the electrocardiograph for the patient;

a computer receiving output from the waveform analyzer, said computer programmed to complete a monitoring cycle in which the computer uses the output from the waveform analyzer to compute a probability of a life threatening cardiac condition based upon the current segment of the patient's ECG waveform; and a control module causing said computer to periodically repeat the monitoring cycle and for each repetition of said monitoring cycle to compute a change-of-condition measure, wherein said change-of-condition measure is calculated by subtracting a computed probability for a previous monitoring cycle from the computed probability for the current monitoring cycle.

* * * * *